United States Patent
Markosyan

(10) Patent No.: US 11,155,888 B2
(45) Date of Patent: Oct. 26, 2021

(54) STEVIA COMPOSITION, PRODUCTION METHOD AND USES

(71) Applicant: PureCircle USA Inc., Oak Brook, IL (US)

(72) Inventor: Avetik Markosyan, Yerevan (AM)

(73) Assignee: PURECIRCLE USA INC., Chicago, IL (US)

( * ) Notice: Subject to any disclaimer, the term of this patent is extended or adjusted under 35 U.S.C. 154(b) by 0 days.

(21) Appl. No.: 15/513,096

(22) PCT Filed: Sep. 24, 2015

(86) PCT No.: PCT/US2015/051943
§ 371 (c)(1),
(2) Date: Mar. 21, 2017

(87) PCT Pub. No.: WO2016/049315
PCT Pub. Date: Mar. 31, 2016

(65) Prior Publication Data
US 2017/0298460 A1 Oct. 19, 2017
US 2020/0032358 A9 Jan. 30, 2020

Related U.S. Application Data

(63) Continuation-in-part of application No. 14/603,941, filed on Jan. 23, 2015, now Pat. No. 9,562,064, which is a continuation of application No. 13/580,098, filed as application No. PCT/US2011/028028 on Mar. 11, 2011, now Pat. No. 8,981,081.

(60) Provisional application No. 62/055,757, filed on Sep. 26, 2014, provisional application No. 61/313,375, filed on Mar. 12, 2010, provisional application No. 61/313,388, filed on Mar. 12, 2010, provisional application No. 61/373,491, filed on Aug. 13, 2010, provisional application No. 61/385,215, filed on Sep. 22, 2010.

(51) Int. Cl.
*A61K 36/28* (2006.01)
*C07H 1/06* (2006.01)
*C07H 15/256* (2006.01)
*A23L 27/00* (2016.01)
*C13K 13/00* (2006.01)

(52) U.S. Cl.
CPC ............ *C13K 13/00* (2013.01); *A23L 27/00* (2016.08); *A61K 36/28* (2013.01); *C07H 1/06* (2013.01); *C07H 15/256* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 4,361,697 A † | 11/1982 | Dobberstein | |
| 4,892,938 A | 1/1990 | Giovanetto | |
| 2007/0082103 A1 | 4/2007 | Magomet et al. | |
| 2008/0300402 A1 | 12/2008 | Yang et al. | |
| 2010/0112175 A1* | 5/2010 | Abelyan | A23C 9/1307 426/548 |
| 2012/0083593 A1 | 4/2012 | Liu et al. | |
| 2014/0004248 A1 | 1/2014 | Zhang et al. | |
| 2014/0199466 A1 | 7/2014 | Pohrte et al. | |

FOREIGN PATENT DOCUMENTS

| | | | | |
|---|---|---|---|---|
| EP | 0302948 B1 | 12/1993 | | |
| WO | 2009140394 | 11/2009 | | |
| WO | 2011112892 A1 † | 9/2011 | | |
| WO | 2012068457 A1 † | 5/2012 | | |
| WO | 2013096420 A1 † | 6/2013 | | |
| WO | WO-2013096420 A1 * | 6/2013 | ............ A23L 2/60 |
| WO | 2013110673 A1 | 8/2013 | | |
| WO | 2014122227 A1 | 8/2014 | | |
| WO | 2015171555 A1 | 11/2015 | | |

OTHER PUBLICATIONS

N.N., "Steviol Glycosides", FAO JECFA Monographs 10 (2010), (Dec. 31, 2010), URL: http://www.fao.org/ag/agn/jecfa-additives/specs/monograph10/additive-442-m10.pdf, (Apr. 5, 2018), XP055464836 [X] 1,5 * the whole document.

* cited by examiner
† cited by third party

*Primary Examiner* — Layla D Berry
(74) *Attorney, Agent, or Firm* — Rachael Casey

(57) ABSTRACT

*Stevia* compositions are prepared from *Stevia rebaudiana* Bertoni extracts. The compositions are able to provide a superior taste profile and can be used as sweeteners, sweetness enhancers, flavors, flavor enhancers in foods, beverages, cosmetics and pharmaceuticals.

4 Claims, No Drawings

STEVIA COMPOSITION, PRODUCTION METHOD AND USES

BACKGROUND OF THE INVENTION

Field of the Invention

The invention relates to a process for producing a purified food ingredient from the *Stevia rebaudiana* Bertoni plant and its use in various food products and beverages.

Description of the Related Art

Nowadays sugar alternatives are receiving increasing attention due to awareness of many diseases in conjunction with consumption of high-sugar foods and beverages. However many artificial sweeteners such as dulcin, sodium cyclamate and saccharin were banned or restricted in some countries due to concerns on their safety. Therefore non-caloric sweeteners of natural origin are becoming increasingly popular. The sweet herb *Stevia rebaudiana* Bertoni, produces a number of diterpene glycosides which feature high intensity sweetness and sensory properties superior to those of many other high potency sweeteners.

The above-mentioned sweet glycosides, have a common aglycon, steviol, and differ by the number and type of carbohydrate residues at the C13 and C19 positions. The leaves of *Stevia* are able to accumulate up to 10-20% (on dry weight basis) steviol glycosides. The major glycosides found in *Stevia* leaves are rebaudioside A (2-10%), stevioside (2-10%), and rebaudioside C (1-2%). Other glycosides such as rebaudioside B, D, E, and F, steviolbioside and rubusoside are found at much lower levels (approx. 0-0.2%).

Two major glycosides—stevioside and rebaudioside A (reb A), were extensively studied and characterized in terms of their suitability as commercial high intensity sweeteners. Stability studies in carbonated beverages confirmed their heat and pH stability (Chang S. S., Cook, J. M. (1983) Stability studies of stevioside and rebaudioside A in carbonated beverages. *J. Agric. Food Chem.* 31: 409-412.)

Steviol glycosides differ from each other not only by molecular structure, but also by their taste properties. Usually stevioside is found to be 110-270 times sweeter than sucrose, rebaudioside A between 150 and 320 times, and rebaudioside C between 40-60 times sweeter than sucrose. Dulcoside A is 30 times sweeter than sucrose. Rebaudioside A has the least astringent, the least bitter, and the least persistent aftertaste thus possessing the most favorable sensory attributes in major steviol glycosides (Tanaka O. (1987) Improvement of taste of natural sweetners. *Pure Appl. Chem.* 69:675-683; Phillips K. C. (1989) *Stevia*: steps in developing a new sweetener. In: Grenby T. H. ed. Developments in sweeteners, vol. 3. Elsevier Applied Science, London. 1-43.) The chemical structure of rebaudioside A is shown in FIG. 1.

Methods for the extraction and purification of sweet glycosides from the *Stevia rebaudiana* plant using water or organic solvents are described in, for example, U.S. Pat. Nos. 4,361,697; 4,082,858; 4,892,938; 5,972,120; 5,962,678; 7,838,044 and 7,862,845.

The invention provides alternative method which introduces new techniques not described in prior art for steviol glycosides purification.

SUMMARY OF THE INVENTION

The present invention is aimed to overcome the disadvantages of existing steviol glycoside purification process.

The invention, in part, pertains to an ingredient comprising steviol glycosides of *Stevia rebaudiana* Bertoni plant. The steviol glycodsides are selected from the group consisting of stevioside, rebaudioside A, rebaudioside B, rebaudioside C, rebaudioside D, rebaudioside E, rebaudioside F, rebaudioside M, rebaudioside N, rebaudioside O, dulcoside A, steviolbioside, rubusoside, as well as other steviol glycosides found in *Stevia rebaudiana* Bertoni plant, glycosylated steviol glycosides and mixtures thereof.

The invention, in part, pertains to a process for producing an ingredient containing rebaudioside A, stevioside, rebaudioside B, rebaudioside C, rebaudioside D, rebaudioside E, rebaudioside F, rebaudioside M, rebaudioside N, rebaudioside O, dulcoside A, steviolbioside, rubusoside, as well as other steviol glycosides found in *Stevia rebaudiana* Bertoni plant, glycosylated steviol glycosides and mixtures thereof.

The starting material is an aqueous or aqueous alcohol solution containing one or more glycosides of steviol-steviol glycosides solution.

The steviol glycosides solution is passed through a resin bed wherein some steviol glycosides are selectively adsorbed to the resin while the other steviol glycosides pass through the resin bed without any significant adsorption. Subsequently the selectively adsorbed steviol glycosides are eluted from the resin to obtain purified steviol glycosides composition.

In another embodiment the steviol glycosides solution is subjected to liquid-liquid extraction using solvent system comprising water and at least one other solvent which is substantially immiscible with water. Some steviol glycosides are selectively extracted into water phase while the other steviol glycosides extract into water immiscible phase. Subsequently the phases are separated to obtain purified steviol glycosides composition.

The compositions can be used as sweeteners, sweetness enhancers, flavors and flavor enhancers in various food and beverage products. Non-limiting examples of food and beverage products include carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables.

Additionally the compositions can be used in drug or pharmaceutical preparations and cosmetics, including but not limited to toothpaste, mouthwash, cough syrup, chewable tablets, lozenges, vitamin preparations, and the like.

The compositions can be used "as-is" or in combination with other sweeteners, flavors and food ingredients.

Non-limiting examples of sweeteners include steviol glycosides, stevioside, rebaudioside A, rebaudioside B, rebaudioside C, rebaudioside D, rebaudioside E, rebaudioside F, rebaudioside M, rebaudioside N, rebaudioside O, dulcoside A, steviolbioside, rubusoside, as well as other steviol glycosides found in *Stevia rebaudiana* Bertoni plant and mixtures thereof, *stevia* extract, glycosylated steviol glycosides, Luo Han Guo extract, mogrosides, glycosylated mogrosides, high-fructose corn syrup, corn syrup, invert sugar, fructooligosaccharides, inulin, inulooligosaccharides, coupling sugar, maltooligosaccharides, maltodextins, corn syrup solids, glucose, maltose, sucrose, lactose, aspartame, saccharin, sucralose, sugar alcohols.

Non-limiting examples of flavors include lemon, orange, fruit, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilisers, thickeners, gelling agents.

The following examples illustrate preferred embodiments of the invention. It will be understood that the invention is not limited to the materials, proportions, conditions and procedures set forth in the examples, which are only illustrative.

EXAMPLE 1

Selective Adsorption by Resin from Aqueous Ethanol Solution

Steviol glycosides were dissolved in 70% v/v aqueous Ethanol to make 10 mL solution containing (w/w) 0.67% Reb D, 0.51% Reb M and 0.82% Reb A. The solution was passed through a column packed with 10 mL Amberlite FPA98C1 resin in OH⁻ form. The resin was washed with 250 mL 70% v/v aqueous Ethanol and then the adsorbed steviol glycosides were eluted with 250 mL of deionized water. Both solutions were analyzed by HPLC and the results are provided below.

| Sample | Content of glycoside, % from TSG* | | |
|---|---|---|---|
| | Reb D | Reb M | Reb A |
| Initial solution | 33.51 | 25.61 | 40.88 |
| 70% Ethanol fraction | 12.51 | 12.05 | 75.44 |
| Water eluate | 51.12 | 43.02 | 5.86 |

*TSG—Total Steviol Glycoside content is calculated as the sum of concentrations of all steviol glycosides It can be seen that the Reb D and Reb M are selectively adsorbed by the resin.

EXAMPLE 2

Treatment of Steviol Glycoside Aqueous Solution by Resin

Steviol glycosides were dissolved in deionized water to make 10 mL solution containing (w/w) 0.67% Reb D, 0.51% Reb M and 0.82% Reb A. The solution was passed through a column packed with 10 mL Amberlite FPA98C1 resin in OH⁻ form. The resin was washed with 250 mL water and then eluted with 250 mL of 70% v/v aqueous Ethanol. Both solutions were analyzed by HPLC and the results are provided below.

| Sample | Content of glycoside, % from TSG* | | |
|---|---|---|---|
| | Reb D | Reb M | Reb A |
| Initial solution | 33.66 | 25.45 | 40.89 |
| Water fraction | 32.94 | 25.06 | 42.00 |
| 70% Ethanol eluate | ND | ND | ND |

*TSG—Total Steviol Glycoside content is calculated as the sum of concentrations of all steviol glycosides
**ND—Not Detected It can be seen that no substantial selective adsorption is observed from aqueous solution.

I claim:

1. A process for decreasing the concentration of Reb A in a steviol glycosides solution, comprising the steps of:

providing a 70% aqueous ethanol solution containing at least Reb A, Reb D and Reb M and having an initial total steviol glycoside (TSG) content and an initial Reb A concentration;

providing at least one resin capable of adsorbing steviol glycosides;

contacting the resin with the 70% aqueous ethanol solution to obtain a resin with at least one selected steviol glycoside adsorbed onto the resin;

washing the resin with 70% aqueous ethanol; and eluting the resin with deionized water to obtain the steviol glycosides solution having a Reb A concentration in a final TSG content that is less than the initial Reb A concentration in the initial TSG content.

2. The process of claim 1, further comprising the step of drying the steviol glycosides solution to obtain a steviol glycoside composition, and adding the steviol glycoside composition to a food ingredient.

3. The process of claim 1, further comprising the step of drying the steviol glycosides solution to obtain a steviol glycoside composition, and adding the steviol glycoside composition to a food, beverage, cosmetic or pharmaceutical product.

4. The process of claim 1, wherein the Reb A concentration in the final TSG content is about 86% less than in the initial TSG content.

* * * * *